(12) United States Patent
Klaptchuk

(10) Patent No.: US 7,501,550 B2
(45) Date of Patent: Mar. 10, 2009

(54) METHOD OF DESTROYING SEEDS

(76) Inventor: Peter Klaptchuk, Box 26030, 1850 Industrial Drive, Regina (CA) S4R 8R7

( * ) Notice: Subject to any disclaimer, the term of this patent is extended or adjusted under 35 U.S.C. 154(b) by 465 days.

(21) Appl. No.: 10/552,680
(22) PCT Filed: Apr. 7, 2004
(86) PCT No.: PCT/CA2004/000524
§ 371 (c)(1), (2), (4) Date: Oct. 10, 2005
(87) PCT Pub. No.: WO2004/089078
PCT Pub. Date: Oct. 21, 2004

(65) Prior Publication Data
US 2006/0207171 A1    Sep. 21, 2006

(30) Foreign Application Priority Data
Apr. 10, 2003    (CA)    ................... 2425029

(51) Int. Cl.
A62D 3/00 (2007.01)
A62D 3/38 (2007.01)
A62D 3/40 (2007.01)
F26B 3/34 (2006.01)
F26B 5/06 (2006.01)
A01C 1/00 (2006.01)
A01G 7/00 (2006.01)
A01H 4/00 (2006.01)

(52) U.S. Cl. .................. 588/320; 588/321; 588/402; 588/405; 34/265; 34/282; 47/58.1 SE; 47/DIG. 9; 47/DIG. 10

(58) Field of Classification Search ............ 588/320, 588/313, 321, 402, 405; 34/245, 259, 265, 34/282; 47/57.6, DIG. 9, 58.1 SE, DIG. 10
See application file for complete search history.

(56) References Cited
U.S. PATENT DOCUMENTS
5,230,160 A * 7/1993 Gross et al. ................. 34/263

(Continued)

FOREIGN PATENT DOCUMENTS
DE    196 05 650 A1    6/1997
DE    19605650 A1    6/1997

(Continued)

OTHER PUBLICATIONS

Luecke et al. "Treatment or stressing of biological substances with microwaves in presence of water vapour for even heating which gently releases aromatic oils, sterilises or modifies germination and growth properties, especially of seeds which may undergo storage before use" Derwent abstract of DE19605650, patent publication Jun. 26, 1997.*

Primary Examiner—Steven Bos
Assistant Examiner—Anthony J Zimmer
(74) Attorney, Agent, or Firm—Adams Intellectual Property Law, P.A.

(57) ABSTRACT

A method of sterilizing seeds comprises heating the seeds to substantially 95° C. or higher and maintaining same at that temperature for substantially 30 minutes. Preferably a combination of steam and microwaves is used to maintain the temperature. Dampening the seeds with steam and water at the start of the process helps the microwaves work more efficiently in maintaining temperature. The method further comprises treating the seeds with ozone which functions both to sterilize seeds as well as to sterilize pathogenic organisms and to degrade residual herbicides, pesticides and like chemicals that may be present in a seed sample. An auger conveyor (7) carries the seed through the process. Temperature sensors (13) monitor the temperature of the seeds and control the speed of the auger so that the seeds are maintained at substantially 95° C. for substantially 30 minutes prior to exiting the output end of the auger conveyor (7). Ozone sensors (17) monitor ozone concentration in order to maintain a concentration of ozone effective to sterilize biological materials as well as to degrade residual chemicals present in seed samples. The auger (7) continuously agitates the seed to expose the seeds to the microwaves and ozone.

24 Claims, 2 Drawing Sheets

U.S. PATENT DOCUMENTS

| | | | |
|---|---|---|---|
| 6,171,625 B1 * | 1/2001 | Denvir et al. | 426/320 |
| 2002/0090268 A1 | 7/2002 | Haller | |
| 5,703,009 A * | 12/1997 | Yvin et al. | 504/116.1 |
| 5,919,390 A * | 7/1999 | Childress | 219/725 |

FOREIGN PATENT DOCUMENTS

| | | |
|---|---|---|
| EP | 1 038 425 A2 | 9/2000 |
| EP | 1038425 A2 | 9/2000 |

\* cited by examiner

METHOD OF DESTROYING SEEDS

This invention is in the field of seeds, and in particular the treatment of seeds to ensure that the seeds do not germinate or reproduce, and to degrade residual chemicals and sterilize pathogens that may be present in a seed sample.

BACKGROUND

Destruction of seeds to prevent germination and reproduction thereof is presently an issue of concern. Genetic modification of seed has received an adverse reaction from a significant portion of the public, concerned about detrimental effects if viable forms of modified seed were to escape into the environment. The possibility that experimental seed could escape into the environment is of such concern that companies engaged in research into such seeds wish to be able to ensure to the public that such escape will not occur.

As a result, companies engaged in seed research cannot simply discard experimental seed that is not needed, but must ensure that the germinal viability of the seed is destroyed. Grinding or crushing seed using methods of the prior art cannot guarantee that some germination can remain viable. Small seeds, such as canola, are especially difficult to pulverize effectively to destroy viability. In addition, grinding or crushing methods are time-consuming, and it is difficult to be confident that the seeds have been adequately destroyed without resorting to additional testing procedures to determine whether any viable seed remains or not. Incineration processes are effective in producing 100% deactivation, but the burning process creates undesirable by-products and emissions are difficult to control and pose a potential environmental hazard. In addition, incineration is expensive in terms of energy costs, and typically makes use of non-renewable energy sources such as natural gas or other fossil fuels. The use of these energy sources further contributes to greenhouse gas emission, as well as to the depletion of finite energy reserves, and is therefore a less than desirable solution.

Although genetically modified seeds are most in the public awareness, it is contemplated that it might also be desired to destroy other conventionally bred seeds, or undesirable seeds found in nature such as various weeds.

Of additional concern is the effect that residual chemical agents such as herbicides and pesticides, commonly applied to commercial crops, may have on the environment and the health of animals and humans. Residues may remain in seed samples increasing the risk to human or animal health when seed products are either consumed or handled.

Likewise, seed samples can harbor pathogens such as molds, bacteria or viruses and other similar biologics that in some cases pose a threat to human health. A known hazard in the field of agriculture is the exposure of farm workers to molds that propagate in seed over time under suitable conditions. Exposure has been associated with asthmatic reactions, and lung infections that can lead to scarring and permanent damage. Farm workers account for 30% of adult respiratory disease and yet only comprise 1% of the population (Storm & Genter (1995), AG-MED-6, North Carolina Cooperative Extension Service).

SUMMARY OF THE INVENTION

It is the object of the present invention to provide a method of destroying seed that ensures that the seeds will not reproduce. It is a further object of the present invention to provide such a method that transforms the seed into a product that may be environmentally safely disposed of.

It is yet another object of the present invention to provide a method of degrading chemicals such as herbicides and pesticides that may be present in a seed sample in order to make the seed safer for handling or consumption.

It is a further object of the present invention to provide a method of sterilizing pathogens such as viruses, bacteria, fungi and protozoans and the like, which may be present in a seed sample.

The invention provides a method of destroying seeds. The seeds are heated to substantially 95° C. and maintained at that temperature for substantially 30 minutes. Preferably a combination of steam and microwaves is used to maintain the temperature. Dampening the seeds with steam at the intake end of the process helps the microwaves work more efficiently in maintaining temperature.

Additionally, the seeds are treated with ozone. Ozone is a reactive species of oxygen, well known in the art to degrade chemical compounds as well as to denature proteins and sterilize pathogenic agents. The ozone, in combination with the steam and microwaves is operative to degrade residual chemicals, and to deactivate the seeds and any associated pathogens present in the seed sample.

An auger conveyor carries the seed through the process. Temperature sensors monitor the temperature of the seeds and control the speed of the auger so that the seeds are maintained at substantially 95° C. for substantially 30 minutes prior to exiting the output end of the auger conveyor. The auger continuously agitates the seed to provide substantially even exposure of all the seeds in the sample to the steam, microwaves and ozone. Conveniently the invention may also include ozone sensors to monitor ozone levels in the seed sample such that a level of ozone effective to degrade residual chemicals and deactivate associated pathogens is present.

Using the controlled speed auger, the process is continuous, allowing for considerable volumes to be processed without intervention or labor requirements, such that automatic oversight of the process is possible.

DESCRIPTION OF THE DRAWINGS

While the invention is claimed in the concluding portions hereof, preferred embodiments are provided in the accompanying detailed description which may be best understood in conjunction with the accompanying diagrams where like parts in each of the several diagrams are labeled with like numbers, and where:

DETAILED DESCRIPTION OF THE ILLUSTRATED EMBODIMENTS

Figure 1:
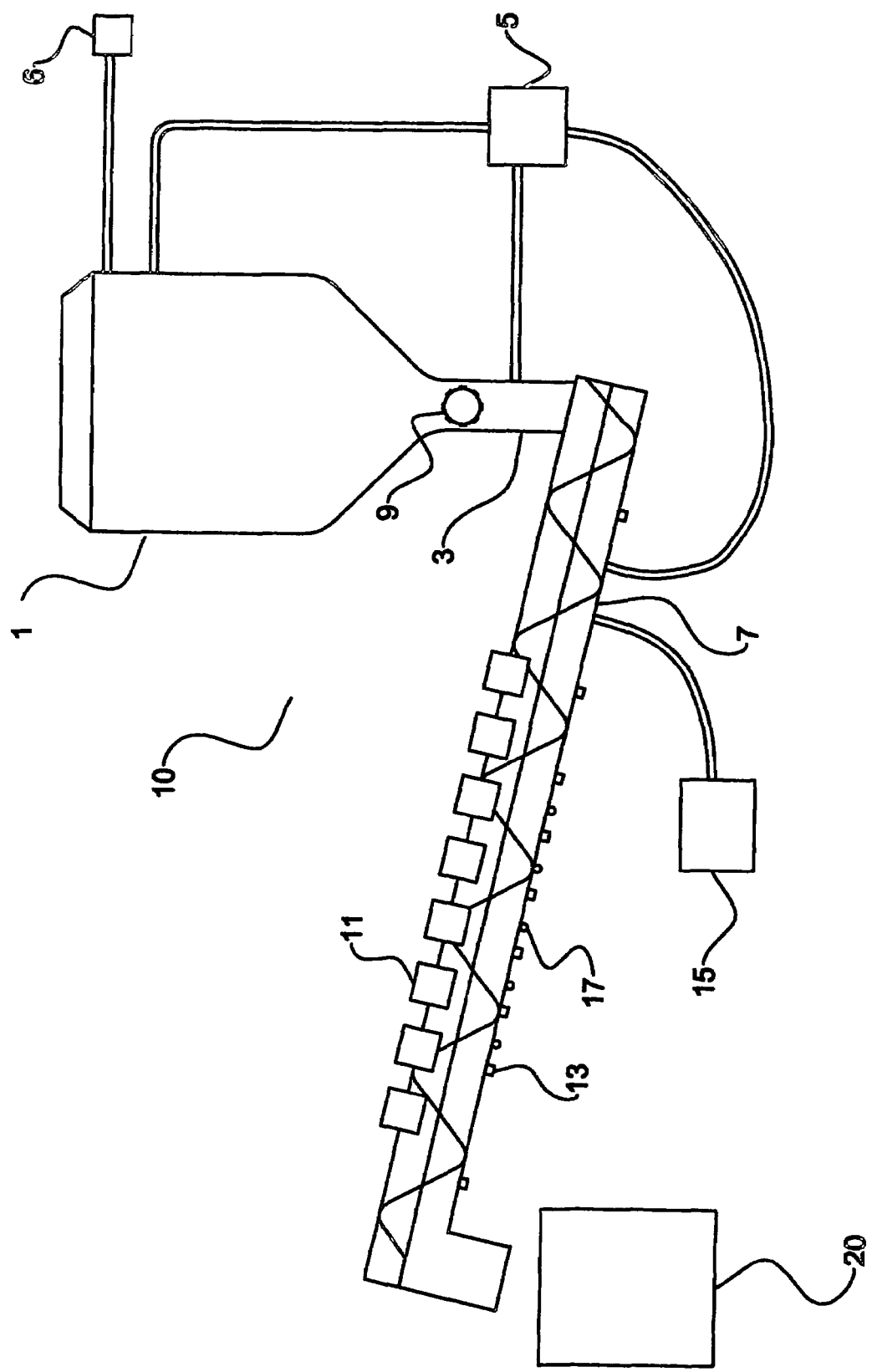
FIG. 1 is a schematic side view of an apparatus for practicing a method of the invention.

FIG. 1 schematically illustrates an apparatus 10 for practicing a method of the invention for destroying seeds to prevent further germination and reproduction from them. The seeds are placed into a hopper 1, where steam at 250-400° C. from a boiler 5 and water from a water source 6 are added to heat and dampen the seeds.

The seeds flow from the hopper into a steam chamber 3. Steam is conducted from the boiler 5 into the steam chamber 3, thereby further raising the temperature of the seed and further wetting the seed somewhat.

A shredder roller 9 may be placed in the bottom of the hopper 1 to break up the seed surface and allow the steam to penetrate the seed more readily. Some seeds are known to have less permeable outer skins that resist dampening, and breaking up the surface helps the steam to penetrate.

At the bottom of the steam chamber 3 the seed flows into the intake of an auger conveyor 7. The auger conveyer 7 comprises a tube that provides an enclosure that can be sealed, as well as an internal auger 8, which rotates to move the seeds through the interior of the enclosure from the intake end to the discharge end. Further steam from the boiler 5 is added near the intake of the auger conveyor 7. At this point the temperature of the seed has been raised to near 95° C. Temperature sensors 13 begin to monitor the temperature of the seeds. Microwave generators 11 further heat the seeds. Once the seed treatment temperature reaches substantially 95° C., a timer mechanism adjusts the rotational speed of the auger such that the seed temperature is maintained at substantially 95° C. or higher for substantially 30 minutes prior to seeds exiting the auger conveyor.

Steam could also be used to maintain the temperature of the seed, for example by encircling the auger with steam lines. It is however preferred to use a series of microwave generators 11 to maintain the seed temperature at substantially 95° C. or higher during the entire time that the seeds are in the enclosure tube. The microwaves work efficiently on the dampened seeds to economically maintain the required temperature, and add their own destructive effects to the process.

If the temperature of the seed in the auger conveyor 7 is sensed by the temperature sensors 13 to be dropping, the auger speed can be reduced so that the seed moves slower through the auger conveyor 7, and thus receives more beat from the microwaves. In this manner each seed is maintained in the auger conveyor 7 for about 30 minutes, and is maintained at the required substantially 95° C. or higher temperature while it is in the auger conveyor 7. In addition to being effective to inactivate seeds such that they are no longer capable of germination, the treatment of seeds as described above is known in the art to be an effective method to substantially reduce the number of viable organisms such as viruses, bacteria, fungi, protozoa and the like.

The invention further comprises an ozone source 15, connected to the tube in proximity of the intake, such that ozone is directly injected into the tube at the beginning of the treatment process so that the seeds are subjected to microwaves and ozone simultaneously. As ozone is well known as being effective to inactivate pathogens such as viruses, bacteria, fungi and protozoa and the like, the use of ozone in the apparatus of the invention augment the sterilizing effects of the microwaves and steam Conveniently, ozone sensors 17 may be included to monitor ozone levels in the enclosure. The output of the sensors can be used via a control mechanism to vary the amount of ozone injected into the enclosure, or to vary the speed of the auger conveyer 7, such that seeds are treated with a sufficient concentration of ozone, for an adequate time, such that the ozone further augments the inactivation of seeds, as well as to substantially degrade herbicides and pesticides, as well as to substantially inactivate pathogens present in the seed sample.

Ozone is further effective to chemically inactivate pesticides and herbicides associated with the seed sample. It has previously shown for example that strong oxidants such as peroxide or ozone are effective in inactivating the herbicide 2,4D (Alfano et al., 2061, Chemical Engineering Journal, 82, 209-218), In the present case, experimental tests were performed to test the method of the invention. Specifically, 220,000 lbs of canola seeds were treated for 30 min at 95° C. After treatment seeds were tested for germination rates, as well as for the presence of the pesticide thiamethoxam. The results of the experiments showed that the rate of germination was zero, and that thiamethoxam was reduced by more than 100-fold, in the treated seed sample. In the experimental tests ozone concentrations of 1500 ppm were used. It is possible with currently available ozone generation systems to achieve ozone levels of 5000 ppm or higher.

Therefore, the data presented herein, when combined with prior studies, indicates that ozone is effective to substantially degrade herbicides and pesticides that may be associated with seed samples. The data fishier demonstrate 1 the invention is effective to render seeds inactive such they are no longer capable of germination. Thus, once the treated seeds exit the auger conveyor 7, seed viability is effectively zero. As a result, the treated seeds exiting the auger conveyor 7 can be safely disposed of. In fact the treated seeds can be readily composted, and sold if desired.

The process is continuous, and requires no intervention. Conveniently, sensors and control mechanisms may be included to monitor temperature and ozone concentration in the closure. The outputs from the sensors are sent to control mechanisms which vary the speed of the auger conveyer 7 in response to temperature and ozone levels, so that seeds are treated for a time sufficient to effectively inactivate seeds, and substantially reduce the levels of pathogens, herbicides or pesticides in the seed sample.

Seed can be fed into the hopper 1 continuously through another auger conveyor sealed to the cover of the hopper 1. Steam is restricted from escaping through the second auger conveyor tube by the auger and the seeds in the tube. The hopper 1 could also be sized to contain a large batch that seldom requires fig. The destroyed seeds can be conveniently be transported away continuously, or collected in a container 20 and removed or disposed of in batches.

Figure 2:
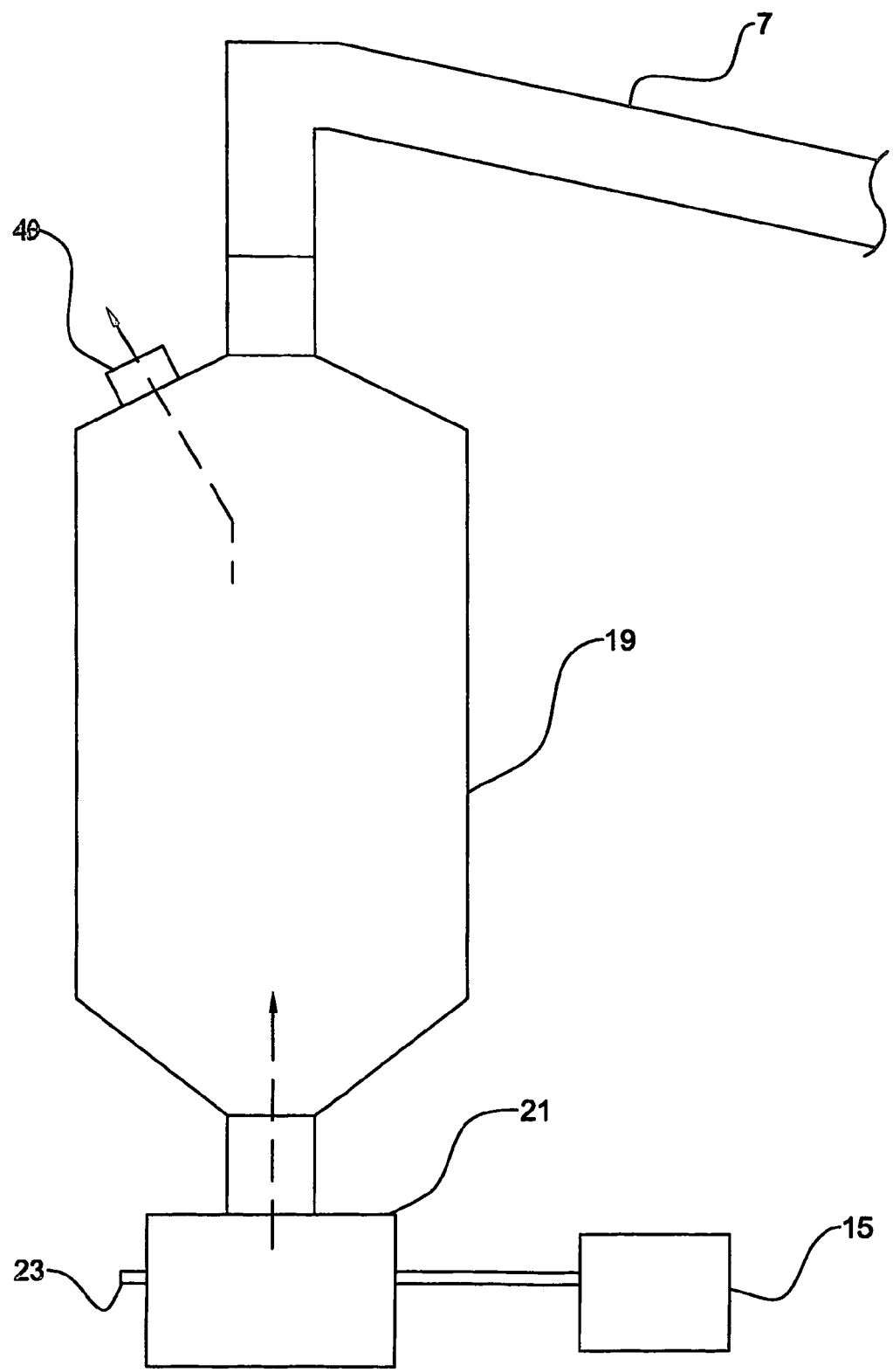
FIG. 2 is a schematic side view of a storage container or silo, where ozone treatment is performed following the treatment of seeds with steam and microwaves. The dashed arrow shows the direction of flow of the drying air and ozone.

Alternatively, instead of or in addition to, introducing ozone into the tube of the auger conveyor 7, the seeds may be discharged from the auger conveyor 7 into a separate container such as the conventional storage silo 19, as illustrated in FIG. 2. The storage silo 19 can be pre-filled with ozone at the desired concentration of 100-5000 ppm. As the seeds fall through the ozone atmosphere, the ozone will have access to the seed surfaces such that the sterilizing properties of the ozone are realized. Providing ozone in the interior of the silo 19 also serves to sterilize the inside walls of the silo, preventing contamination of the seeds.

The auger conveyor 7 can be adapted to discharge the seeds into a plurality of silos 19 such that the continuity of the process can continue uninterrupted as the silos 19 are filled and then emptied intermittently.

Further, a seed dryer 21 might be desirable to dry the seed material, which is damp from exposure to steam and water, if it is to be stored for any length of time prior to disposal. The drying process can be initiated either during or after filling the silo 19. Conveniently ozone from an ozone source 15 is mixed with air from an air inlet 23 and the air: ozone mite is passed through the seeds in the conventional drying process, and out through a vent 40.

By providing ozone during the drying process, an advantage is gained in that ozone will prevent the growth of any contaminating organisms during the time the seed is being dried for further processing or storage.

The foregoing is considered as illustrative only of the principles of the invention. Further, since numerous changes and modifications will readily occur to those skilled in the art, it is not desired to limit the invention to the exact construction and operation shown and described and accordingly, all such suitable changes or modifications in structure or operation which may be resorted to are intended to fail within the scope of the claimed invention.

The invention claimed is:

1. A method of treating a seed sample to prevent germination of seeds in the sample and to render seeds in the seed sample safe for disposal comprising:
    subjecting the seed sample to a combination of steam and microwaves operative to heat the seed sample to a treatment temperature effective to inactivate seeds in the seed sample to prevent germination and reproduction of the seeds; and
    subjecting the seed sample to an effective ozone concentration operative to degrade herbicides and pesticides present in the seed sample and operative to inactivate pathogenic organisms present in the seed sample, wherein the seeds are subjected to microwaves and ozone simultaneously.

2. The method of claim 1 wherein the treatment temperature is greater than 95° Celsius.

3. The method according to claim 1 wherein the seed sample is maintained at the treatment temperature for at least 25 minutes.

4. The method according to claim 1 wherein the effective ozone concentration is between 100 and 5000 parts ozone per million parts air (ppm).

5. The method according to claim 1 wherein the herbicide or pesticide is one of 2, 4D or thiamethoxam.

6. The method according to claim 1, wherein the pathogens comprise at least one of viruses, bacteria, fungi, or protozoa.

7. The method of claim 1 wherein the seed sample comprises genetically modified seeds.

8. The method of claim 1, and further comprising composting the treated seeds.

9. A method of treating a seed sample to prevent germination of seeds in the sample and to render seeds in the seed sample safe for disposal comprising:
    subjecting the seed sample to a combination of steam and microwaves operative to heat the seed sample to a treatment temperature effective to inactivate seeds in the seed sample to prevent germination and reproduction of the seeds; and
    subjecting the seed sample to an effective ozone concentration operative to degrade herbicides and pesticides present in the seed sample and operative to inactivate pathogenic organisms present in the seed sample, wherein the seeds are subjected to microwaves first and then subjected to ozone.

10. The method of claim 9, wherein the treatment temperature is greater than 95° Celsius.

11. The method according to claim 9, wherein the seed sample is maintained at the treatment temperature for at least 25 minutes.

12. The method according to claim 9, wherein the effective ozone concentration is between 100 and 5000 parts ozone per million parts air (ppm).

13. The method according to claim 9, wherein the herbicide or pesticide is one of 2, 4D thiamethoxam.

14. The method according to claim 9, wherein the pathogens comprise at least one of viruses, bacteria, fungi, or protozoa.

15. The method of claim 9 wherein the seed sample comprises genetically modified seeds.

16. The method of claim 9, and further comprising composting the treated seeds.

17. A method of treating a seed sample to prevent germination of seeds in the sample and to render seeds in the seed sample safe for disposal comprising:
    subjecting the seed sample to a combination of steam and microwaves operative to heat the seed sample to a treatment temperature effective to inactivate seeds in the seed sample to prevent germination and reproduction of the seeds;
    subjecting the seed sample to an effective ozone concentration operative to degrade herbicides and pesticides present in the seed sample and operative to inactivate pathogenic organisms present in the seed sample;
    and further passing the seeds through a shredder roller to break open the seeds before subjecting the seed sample to the combination of steam and microwaves.

18. The method of claim 17, wherein the treatment temperature is greater than 95° Celsius.

19. The method according to claim 17, wherein the seed sample is maintained at the treatment temperature for at least 25 minutes.

20. The method according to claim 17, wherein the effective ozone concentration is between 100 and 5000 parts ozone per million parts air (ppm).

21. The method according to claim 17, wherein the herbicide or pesticide is one of 2, 4D thiamethoxam.

22. The method according to claim 17, wherein the pathogens comprise at least one of viruses, bacteria, fungi, or protozoa.

23. The method of claim 17, wherein the seed sample comprises genetically modified seeds.

24. The method of claim 17, and further comprising composting the treated seeds.

* * * * *